(12) United States Patent
Swonger

(10) Patent No.: US 8,315,464 B2
(45) Date of Patent: Nov. 20, 2012

(54) METHOD OF PORE DETECTION

(75) Inventor: Claron Swonger, Saline, MI (US)

(73) Assignee: Coherix, Ann Arbor, MI (US)

( * ) Notice: Subject to any disclaimer, the term of this patent is extended or adjusted under 35 U.S.C. 154(b) by 961 days.

(21) Appl. No.: 12/364,851

(22) Filed: Feb. 3, 2009

(65) Prior Publication Data

US 2009/0202154 A1   Aug. 13, 2009

Related U.S. Application Data

(60) Provisional application No. 61/026,746, filed on Feb. 7, 2008.

(51) Int. Cl.
G06K 9/00 (2006.01)
G06K 9/32 (2006.01)
F21V 7/04 (2006.01)
G01N 21/00 (2006.01)

(52) U.S. Cl. ........ 382/190; 382/108; 382/286; 362/612; 356/237.2

(58) Field of Classification Search .............. 382/108, 382/254, 260, 266, 307, 308, 222, 225, 194–196, 382/298, 100, 109, 126–219, 286; 250/559.01, 250/559.04, 559.06, 559.08, 559.4, 559.42, 250/559.44, 559.48, 559.05; 348/86, 88, 348/90, 92, 125–134; 356/73.1, 239, 240, 356/237, 394, 371, 445, 446, 429–431, 237.1, 356/237.2, 239.1, 237.6, 239.7, 243.4; 362/545, 362/555, 611, 612, 800
See application file for complete search history.

(56) References Cited

U.S. PATENT DOCUMENTS

| | | | | |
|---|---|---|---|---|
| 3,748,047 A | * | 7/1973 | Millgard et al. | 356/431 |
| 3,922,545 A | * | 11/1975 | Gibbons et al. | 250/303 |
| 5,809,162 A | * | 9/1998 | Csipkes et al. | 382/108 |
| 6,462,813 B1 | * | 10/2002 | Haven et al. | 356/237.2 |
| 6,891,672 B2 | * | 5/2005 | Whitehead et al. | 359/443 |
| 7,570,794 B2 | * | 8/2009 | Swanger et al. | 382/141 |
| 7,834,992 B2 | * | 11/2010 | Yoshida et al. | 356/237.2 |
| 2007/0236689 A1 | * | 10/2007 | Yoshida et al. | 356/237.2 |
| 2009/0325323 A1 | * | 12/2009 | Ueno et al. | 438/10 |
| 2010/0028567 A1 | * | 2/2010 | Suizu et al. | 428/1.32 |

* cited by examiner

Primary Examiner — Sheela Chawan
(74) Attorney, Agent, or Firm — Rodney T. Hodgson

(57) ABSTRACT

The a surface of an object is illuminated in sequence with a number of light beams, each of which is nearly tangential to the surface. Images of the surface are recorded for each light beam, and the images are analyzed to identify features such as depressions in the surface.

11 Claims, 6 Drawing Sheets

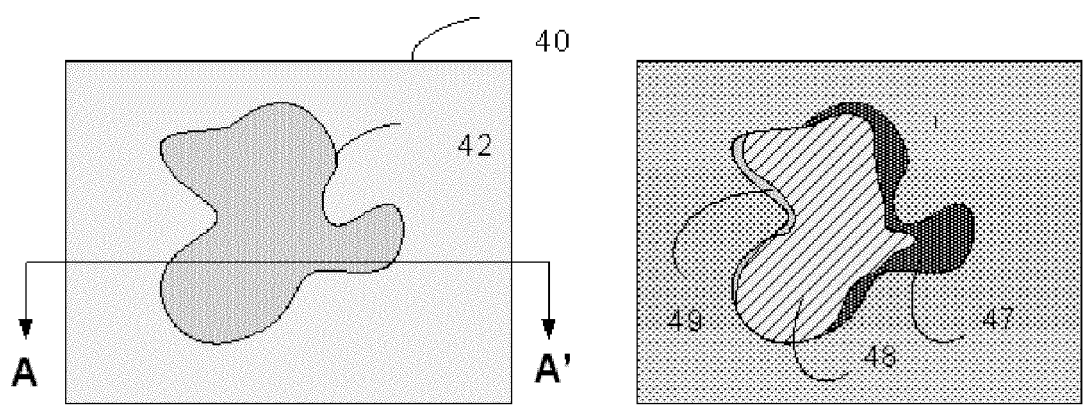
Fig. 4A
Fig. 4c
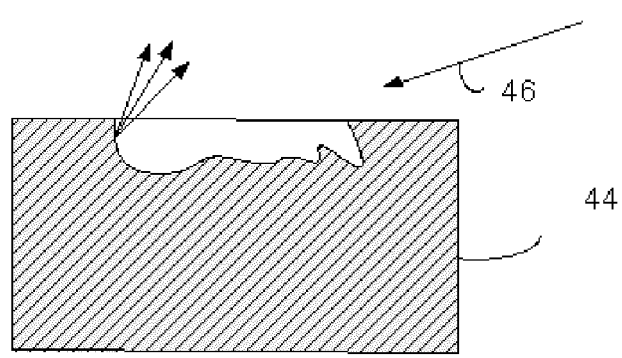
Fig. 4B

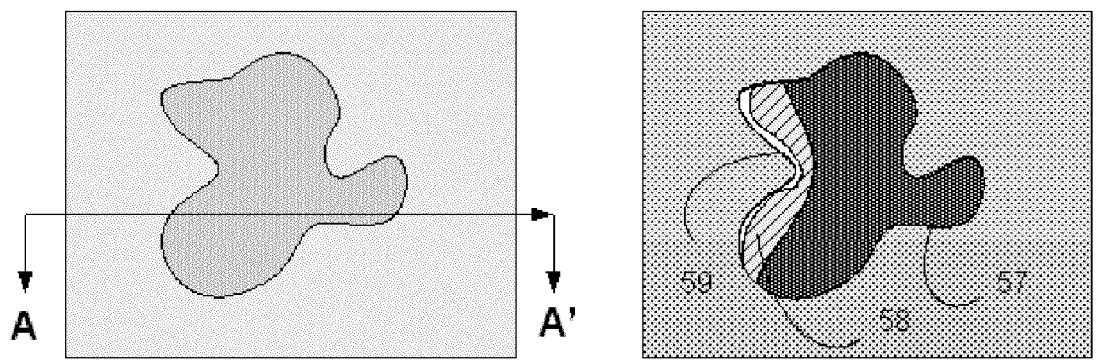
Fig. 5A
Fig. 5c
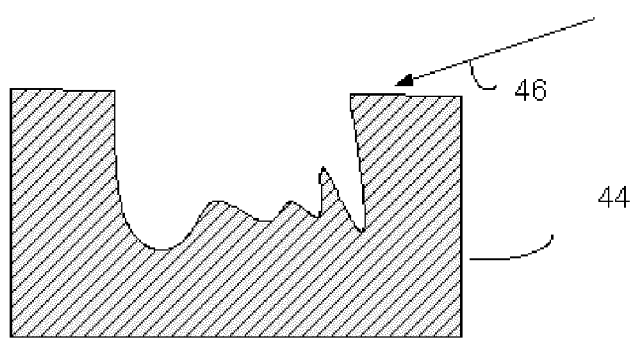
Fig. 5B

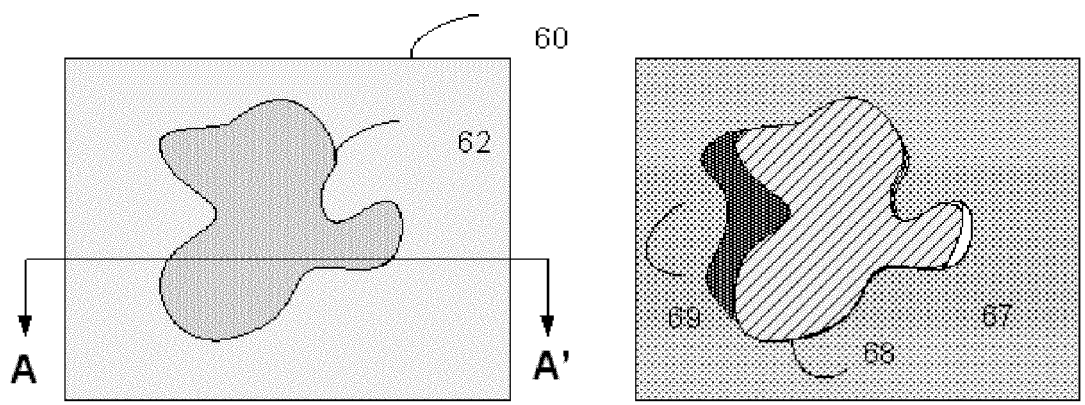
Fig. 6A
Fig. 6c
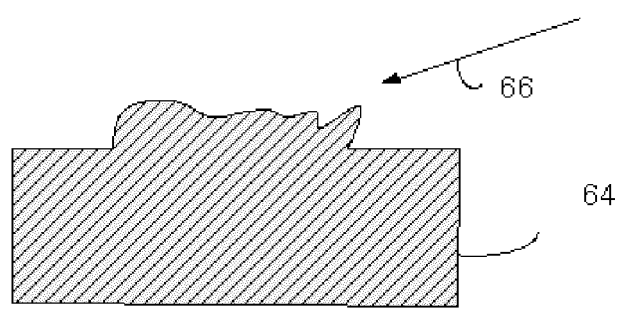
Fig. 6B

METHOD OF PORE DETECTION

FIELD OF THE INVENTION

The field of the invention is the field of optical inspection of defects on the surface of objects.

OBJECTS OF THE INVENTION

It is an object of the invention to identify defects on the surface of an object. It is further object of the invention to classify defects as depressions or protrusions of the surface. It is further object of the invention to measure the length, width, and depth of such depressions or protrusions.

BRIEF DESCRIPTION OF THE FIGURES

FIGS. 4A and 4B show plan and cross sectional elevation sketches of a shallow pore.

FIG. 4C shows an sketch the image taken normally of the shallow pore illuminated obliquely.

FIGS. 5A and 5B show plan and elevation of a cross sectional elevation sketch of a deep pore.

FIG. 5C shows a sketch of the image taken normally of a deep pore illuminated obliquely.

FIGS. 6A and 6B show plan and cross sectional elevation sketches of a raised surface feature.

FIG. 6C shows a sketch of the image taken normally of a raised surface feature illuminated obliquely.

DETAILED DESCRIPTION OF THE INVENTION

Figure 1A:
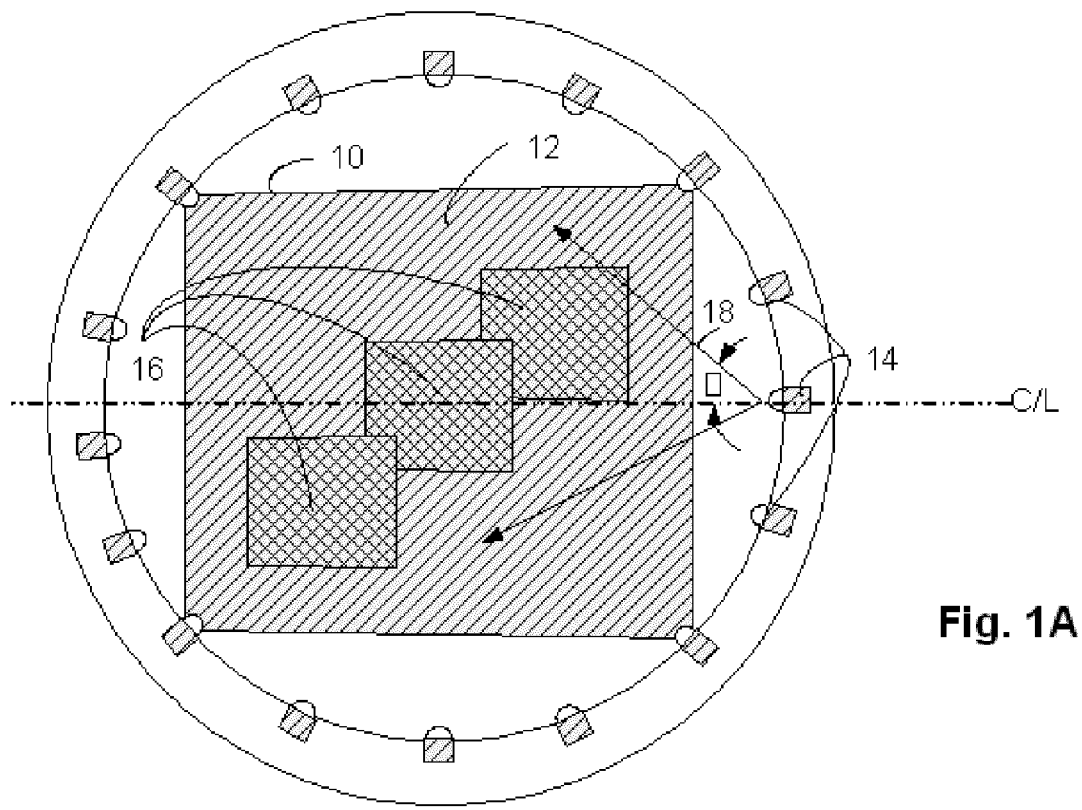
FIGS. 1A and 1B show plan and elevation views of the lighting system of the invention.
Figure 1B:
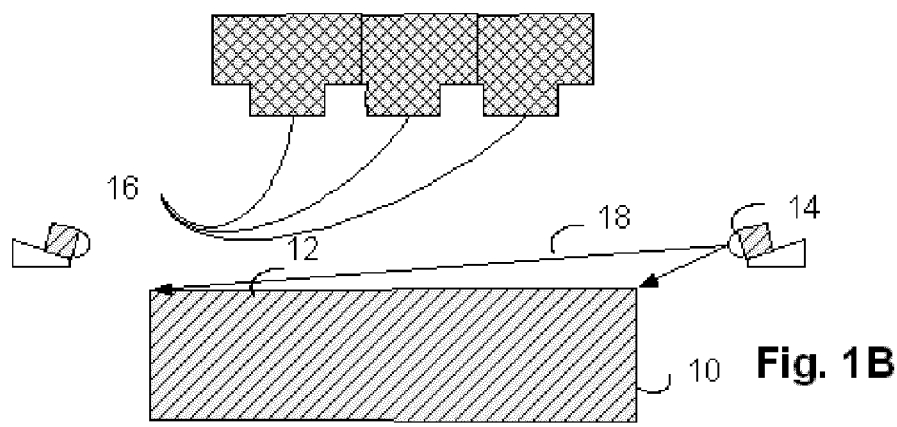

Pore detection is a major problem in parts which are machined from castings. Typically, metal pored into a mold will have or produce bubbles of gas, which when the liquid metal solidifies, produce voids. Solid particles in the molten metal can also produce pores in the part. When the casting is machined, the pores will be opened, and the surface will be imperfect and, for instance, will not hold a seal under pressure if the surface is to be used as a sealing surface.

Optical inspection of such surfaces is difficult, because the parts will have tool marks, and can have in addition blemishes like dirt particles on the surface, stains, burrs, gouges, dings in the surface, scratches in the surface, etc. The part should be washed to remove dirt ad particles, but it is very difficult to remove all the classes of surface imperfections, and many such artifacts such as dirt and particles remaining after washing should be identified and ignored. Some imperfections, such as shallow depressions are not important and can be ignored. However, scratches larger than a defined width and depth can make the part unusable, just as pores or a collection of pores.

Interferometric optical imaging is useful for detecting the height variation of the surface, and is usually performed on a flat machined surface where the tool marks are the only feature in the portions of the surface that are of interest. The plane waves of the interferometric illumination system are directed substantially normal to the surface, and the surface is rough enough to scatter light to produce an image, but not so rough that the light is scattered isotropically. However, if a hole or scratch occurs in the surface, the bottom of the hole will have different scattering and reflective properties, and there may also be multiple reflections which throw light back to the measuring system, and the light phases are scrambled and difficult to interpret.

Previous computerized vision systems, on the other hand, are confused by dirt, changes in reflectivity or absorption of the light, and have difficulty in determining if a feature is a local depression or a rise above the local surface.

The present invention uses a computerized vision system which uses a number of individually controlled light sources to sequentially shine light from different azimuthal directions at oblique angles to the surface. The depressions and hillocks on the surface have different signatures, and can be used to differentiate between types of surface defects. A multiplicity of images is captured by one or more imaging sensors that observe the surface from one or more directions that are very approximately normal to the surface. Each image is captured with a different one or more of the oblique light sources illuminated. The set of images thus created are all aligned geometrically and they can therefore be analyzed as a set in which any given pixel in any of the images corresponds to the same point on the surface as the corresponding pixel of all other images.

Information is retained such that the location of the illumination source and the directional pattern of the illumination is known for each of the multiple images that are captured and this information is used in analyzing the patterns of shadowed portions and the brightly lit portions of all observed features in the set of aligned images.

Generally, a set of similar parts will be analyzed, and information is available defining the correct overall shape of the part, as well as locations of bored or cast holes and other features is known. Such features are useful in comparing part to part, and in segmenting the images taken to remove pixels outside the area of interest on the part. The computer calculation required for the pixel by pixel comparison is therefore much reduced.

FIGS. 1A and B show plan and elevation views of the lighting system. The surface 10 of an object 12 is illuminated in sequence by one of a plurality of illuminations sources 14. Source 14 shines light at an oblique angle to the surface 12. Imaging systems such as a camera 16 or a plurality of cameras 16 capture light scattered approximately normal to the surface to produce a sequence of images of the surface 12 for each of the illumination sources 14. Light rays 18 are shown diverging from one source 14 to illuminate a large portion of the surface 12. The angle θ that each light ray 18 makes with a centerline drawn through a particular light source 14 and the center of the part will vary over the entire surface of the part, but a computer can keep track of the direction of illumination, and also of the angle between the horizontal and the light ray 18, and the information used to classify features as noted below.

Figure 2:
FIG. 2 shows an image of a pore.

FIG. 2 shows an image of a pore having dimensions approximately 2.1 mm by 0.7 mm which was photographed from a direction approximately normal to the surface while it was irradiated at an oblique angle by a beam of sunlight from the direction indicated by the arrow superimposed upon that Figure.

Figure 3:
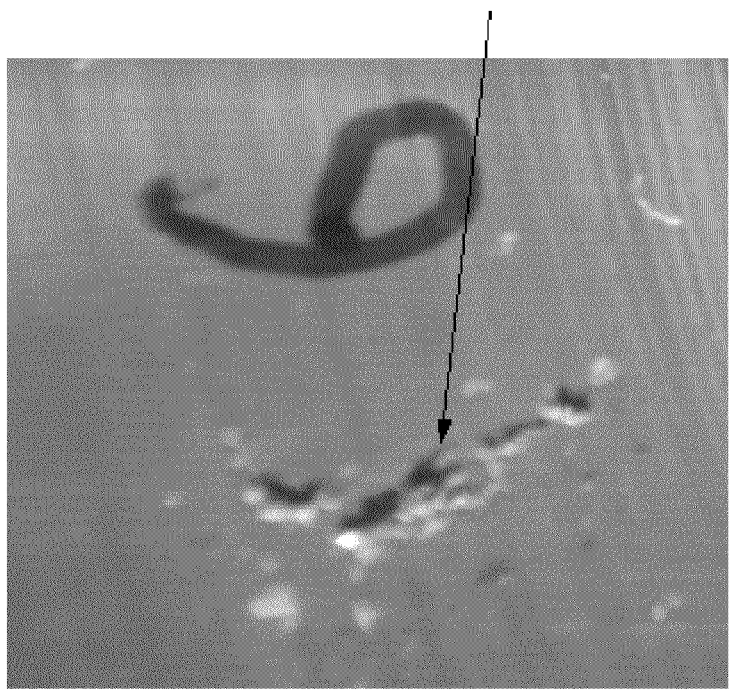
FIG. 3 shows an image of a pore cluster.

FIG. 3 shows an image of a pore cluster having dimensions approximately 5.0 mm by 0.6 mm which was photographed from a direction approximately normal to the surface while it was irradiated at an oblique angle by a beam of sunlight from the direction indicated by the arrow superimposed upon that Figure.

FIGS. 4A and B show plan and cross sectional elevation sketches of a shallow pore.

FIG. 4C shows an sketch the image taken normally of the shallow pore illuminated obliquely.

FIGS. 5A and B show plan and elevation of a cross sectional elevation sketch of a deep pore.

FIG. 5C shows a sketch of the image taken normally of a deep pore illuminated obliquely.

FIGS. 6A and B show plan and cross sectional elevation sketches of a raised surface feature.

FIG. 6C shows a sketch of the image taken normally of a raised surface feature illuminated obliquely.

Figure 7:
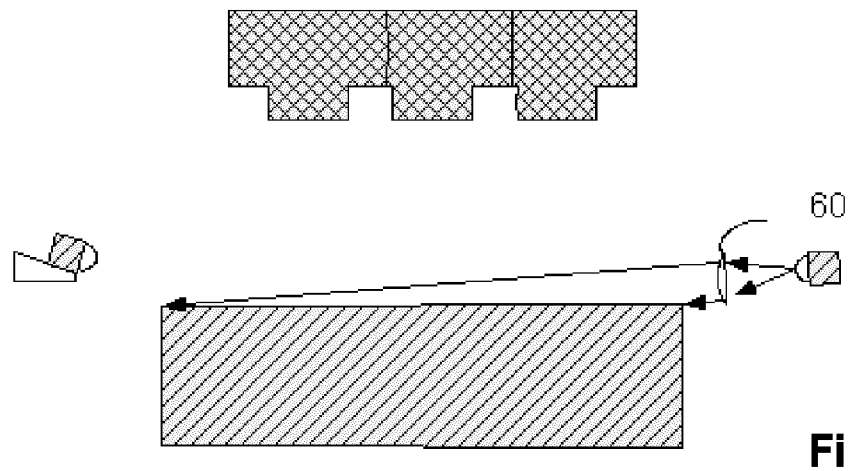
FIG. 7 shows an LED with a lens which changes the normal LED pattern into a parallel beam.

FIG. 7 shows an LED with a lens which changes the normal LED pattern into a parallel beam of sufficient width that the beam illuminates the entire dimension of the part. A cylindrical lens, for example, of 3 cm vertical dimension shown in the figure will illuminate a 300 mm part at the angles and dimensions sketched.

Figure 8:
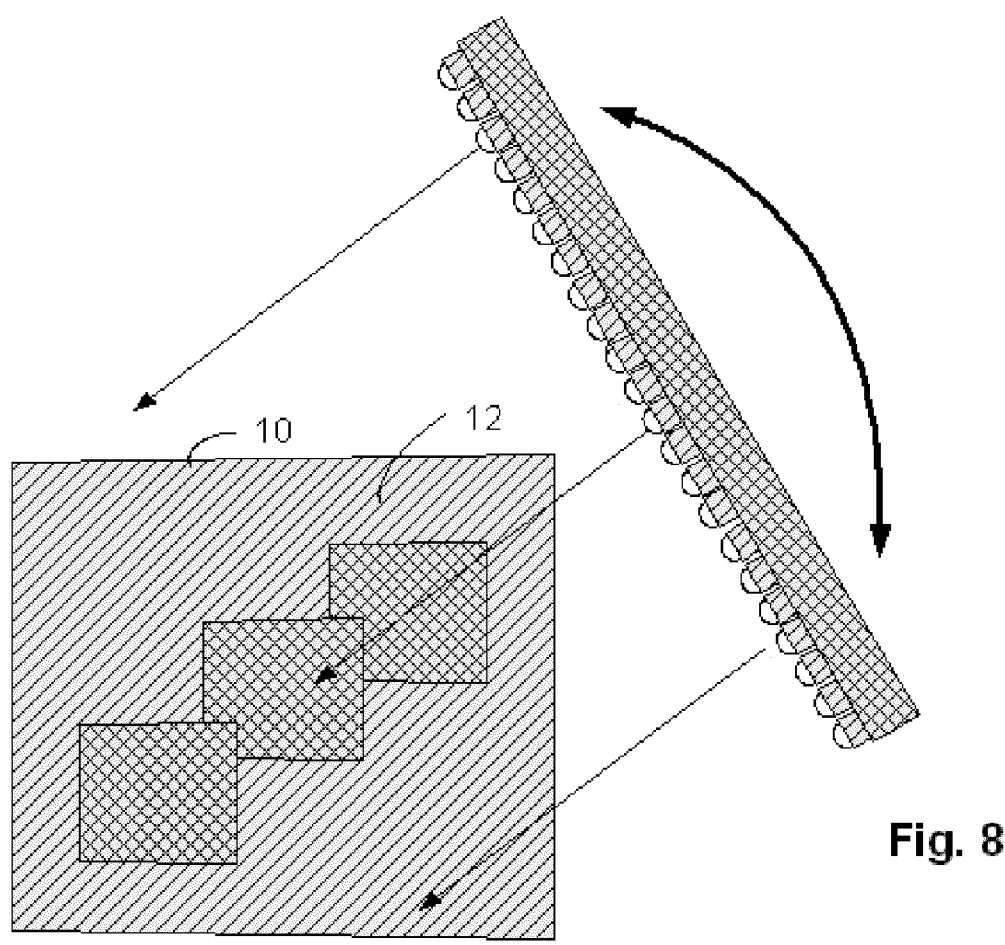
FIG. 8 shows a sketch of a bank of LEDs.

FIG. 8 shows a sketch of a bank of LEDs which can be pivoted about the center of the part to produce parallel light illumination from many directions. Each LED may be configured to produce the required divergence in each of the vertical and horizontal directions. The bank of LEDs may be replaced with a fiber optic bundle, with the ends of the fibers aligned parallel together in a line. A cylindrical lens may also be used to control the divergence of the light. The bank of LEDs may be replaced with a bundle of fibers, illuminated at one end with a conventional light source, one or more LEDs, lasers, etc. The other end of the optical fiber bundle is arranged in a line to produce a linear light source with diverging light of a specified divergence. In all cases, lenses, diffusers, and baffles can be used by one of skill in the art to control the illumination beam pattern.

An object 40 in FIG. 4A has a feature 42 on the surface. Light 46 is shone obliquely on to the surface of the object 40 shown in elevation 44 where the cut is taken across line A-A' An image shown in FIG. 4c shows a shadow 47 on the right hand side of the feature as observed in the image, an illuminated section 48 of the bottom of the feature, and a brightly lighted region 49 on the left hand side of the feature as observed in the image. Note that the total area of the feature as observed in the image does not change significantly as the illumination is changed from side to side and top to bottom of the image. When the light is shifted to impact from the left, the brightly lighted region shifts to the other side of the feature as observed in the image from FIG. 4C. The area of the shadow gives a measure of the approximate depth of the feature, as shown in FIGS. 5A-C.

In FIG. 6, a raised feature shows that the feature as observed in the image has greater area than feature as observed in an image taken in normally distributed light. The light and shadow are also on opposite sides of the feature as observed in the image as would be in a depression in the surface.

If the feature as observed is a depression, and the image shows no shadow, the angle formed by the intersection of the surface of the depression and the surface is less than the oblique angle of the light shining on the surface. Therefore a simple variation in surface reflection that shows no shadows and therefore no significant depth or height would not exhibit significantly different signatures as the illumination azimuthal direction is varied using different illuminators in the illuminator array.

By examining all of the images taken from a multiplicity of different oblique illumination azimuthal directions considering the above factors, the perimeter of each surface feature that is a depressed such as a pore, or a raised feature such as a dirt particle, or neither depressed nor raised such as a reflectance blemish, can be identified and the depth or height profile of each said feature can be estimated. Thereby different types of blemishes are identified by class as well as measured in 2 dimensions of the surface, as well as approximately measured in the depth. These identifications are then compared to the specifications for the allowable number, spacing, sizes, types and patterns of blemishes in any class in order to accept or reject the object of which the observed surface is a part.

In the specific case of pore detection, the set of captured images and the associated information defining the direction of illumination for each said image allow pores to be discriminated from raised features because the perimeter points of a pore feature closest to the illumination source will be shadowed while the perimeter points furthest from the illumination source will be brightest. The inverse is true for raised features. Shallow surface features such as dings and 2-dimensional blemishes will exhibit neither of these characteristics.

We claim:

1. A method for distinguishing features in images of the surface of an object, comprising:
   a) illuminating a surface of an object in sequence with a plurality of light beams, each of the plurality of light beams nearly tangential to the surface, and each of the plurality of light beams illuminating the surface of the object from a different direction;
   b) imaging the surface with an imaging system to produce a plurality of images for each of the plurality of light beams; then
   c) analyzing the plurality of images to identify a feature, the feature being a depression in the surface, wherein the depression has a depth greater than a specified depth, and wherein the depression has a length, a width, or an area greater than a specified dimension.

2. The method of claim 1, wherein the step of analyzing comprises distinguishing a depression from a bump on the surface.

3. The method of claim 1, wherein the step of analyzing comprises distinguishing a depression from a stain on the surface.

4. The method of claim 1, wherein the step of analyzing comprises categorizing each feature as belonging one of a plurality of classes, at least one of the classes being a class of pores.

5. The method of claim 4, wherein the plurality of classes consists of the classes of pores, burrs, dings, scratches, gouges, dirt and stains.

6. The method of claim 1, wherein the step of analyzing comprises identifying a dark area in the image of the feature and a bright area in the image of the feature, wherein the bright area is on the opposite side of the dark area from a source of the illuminating light beam.

7. The method of claim 1, wherein the step of analyzing comprises comparing the area of a dark area in the image of the feature with the total area of the feature.

8. A method for distinguishing features in images of the surface of an object, comprising:
   a) illuminating a surface of an object in sequence with a plurality of light beams, each of the plurality of light beams nearly tangential to the surface, and each of the plurality of light beams illuminating the surface of the object from a different direction;
   b) imaging the surface with an imaging system to produce a plurality of images for each of the plurality of light beams; then c) comparing the brightness of each pixel in each of the plurality of images with corresponding pixels of each of the plurality of images;
d) identifying pixels comprising perimeter pixels of a feature;
e) deciding whether the feature is a depression having a dimension greater than a specified dimension on the basis of a criterion based on the comparison of the brightness of each pixel.

9. The method of claim 8, wherein the step of comparing comprises calculating, for each particular pixel, the ratio of the brightness of that pixel with an averaged brightness of that pixel in each of the plurality of images.

10. The method of claim 8, wherein the pixels satisfying a comparison criterion are further analyzed to connect geometrically closed subsets of said perimeter pixels spatially to produce one or more estimated closed perimeter contours of local spatial surface features such as a bumps, dirt specks or pores.

11. The method of claim 10, wherein the number of identified perimeter pixels that are dark for illumination from the one side of an enclosed dark area is compared to the number of identified perimeter pixels that are bright in the deciding step e).

* * * * *